(12) United States Patent
Lu et al.

(10) Patent No.: US 8,143,040 B2
(45) Date of Patent: Mar. 27, 2012

(54) PROCESS FOR WHOLE CELL SACCHARIFICATION OF LIGNOCELLULOSES TO SUGARS USING A DUAL BIOREACTOR SYSTEM

(75) Inventors: Jue Lu, Okemos, MI (US); Benedict Okeke, Montgomery, AL (US)

(73) Assignee: Metna Co, Lansing, MI (US)

( * ) Notice: Subject to any disclaimer, the term of this patent is extended or adjusted under 35 U.S.C. 154(b) by 496 days.

(21) Appl. No.: 12/379,569

(22) Filed: Feb. 25, 2009

(65) Prior Publication Data
US 2009/0221050 A1 Sep. 3, 2009

Related U.S. Application Data (60) Provisional application No. 61/067,724, filed on Mar. 1, 2008.

(51) Int. Cl.
*C12P 7/10* (2006.01)
(52) U.S. Cl. ............... 435/165; 435/14; 435/18; 435/41
(58) Field of Classification Search ............... 435/14, 435/18, 41, 165; 525/408, 423
See application file for complete search history.

(56) References Cited

U.S. PATENT DOCUMENTS

| | | |
|---|---|---|
| 4,628,029 A | 12/1986 | Eveleigh et al. |
| 5,348,871 A | 9/1994 | Scott et al. |
| 5,628,830 A | 5/1997 | Brink |

OTHER PUBLICATIONS

Bevan, M. W. and M. C. R. Franssen (2006). "Investing in green and white biotech." Nature Biotechnology 24(7): 765-767.
Biely, P. (1985). "Microbial xylanolytic systems." Trends in Biotechnology 3(11): 286-290.
Knowles, J., P. Lehtovaara, et al. (1987). "Cellulase Families and Their Genes." Trends in Biotechnology 5(9): 255-261.
Li et al. (1997). "Two cellulases, CelA and CelC for a cellulase-hemicellulase complex." Applied and Environmental Microbiology 63(12): 4721-4728.
Wenzel et al. (2002). "Aerobic and facultatively anaerobic cellulolytic bacteria from the gut of the termite *Zootermopsis angusticollis*." J. of Appl. Microbio. 92(1): 32-40.
Wyman, C. E. (2007). "What is (and is not) vital to advancing cellulosic ethanol." Trends in Biotechnology 25(4): 153-157.

*Primary Examiner* — Chih-Min Kam (57) ABSTRACT

The present invention describes a process for saccharification of lignocelluloses to sugars using whole microbial cells, which are enriched from cultures inoculated with paper mill waste water, wood processing waste and soil. A three-member bacterial consortium is selected as a potent microbial inocula and immobilized on inedible plant fibers for biomass saccharification. The present invention further relates the design of a dual bioreactor system, with various biocarriers for enzyme immobilization and repeated use. Sugars are continuously removed eliminating end-product inhibition and consumption by cell.

7 Claims, 8 Drawing Sheets

PROCESS FOR WHOLE CELL SACCHARIFICATION OF LIGNOCELLULOSES TO SUGARS USING A DUAL BIOREACTOR SYSTEM

CROSS-REFERENCE TO RELATED APPLICATIONS

This application claims the benefit of U.S. Provisional Application No. 61/067,724, filed on Mar. 1, 2008. The disclosure of the above application is incorporated herein by reference.

SPONSORSHIP

Subject matter described herein was developed with SBIR funding provided by the United States Government under Grants from the Department of Energy (DE-FG-02-07ER84872). The U.S. Government may have certain rights to the invention.

INTRODUCTION

Over dependence on fossil fuel has spurred research on alternative energy. Inedible plant materials such as grass and corn stover are abundant renewable natural resources that can be transformed into biofuel. Plant materials are composed largely of lignocelluloses, which is a polymer of cellulose, hemi-celluloses (mainly xylans) and lignin. The greatest challenge to the wide-spread use of plant biomass in fermentation is the complexity of the lignocellulosic cell wall components that form the bulk of biomass (Bevan and Franssen 2006). Cellulose, a linear glucose polymer, is the principal structural polysaccharide in plants, the most abundant constituent of lignocelluloses. Hemicelluloses are heteropolymers of a range of pentose sugars, primarily xylose and arabinose, as well as hexose sugars such as galactose, mannose, other sugars, and uronic acids (Biely 1985; Okeke and Obi 1994). Microbial degradation of lignocellulose components is achieved by a variety of microbial enzymes (Li et al. 1997; Wenzel et al. 2002). Cellulose is hydrolyzed by the synergistic action of cellobiohydrolases (exocellulases), endoglucanases (endocellulases) and β-glucosidases (Knowles et al. 1987). Xylans are degraded by an array of hydrolases such as exoxylanases, endoxylanases, β-xylosidases, acetylxylan esterases, arabinofuranosidases and glucoronidases (Biely 1985). Lignin is a large, cross-linked macromolecule with molecular mass in excess of 10,000 amu, largely hydrophobic and aromatic in nature. The lignin component of the polymer is degraded by peroxidases and phenol oxidases notably lactases.

Enzymatic hydrolysis of lignocelluloses has been a common method for converting biomass to fermentable sugars. For example, U.S. Pat. No. 4,628,029 described a method for the enzymatic saccharification of a cellulosic substrate to glucose which utilizes fermentation of the substrate with the cellulase enzyme complex-producing, thermophilic microorganism *Microbispora bispora* Rutgers P&W and its mutants; U.S. Pat. No. 5,628,830 developed a method of producing sugars from biomass using enzymatic hydrolysis with very fine particle size after pre-hydrolysis of the hemicellulosic content; and Scott, et al. described a process for enzymatic hyodrolysis of paper in U.S. Pat. No. 5,348,871, with cellulase produced from a continuous bioreactor utilizing immobilized microorganisms. Problems of enzymatic conversion of inedible fiber to sugars include incomplete synergistic enzymes, need for pretreatment, end-product inhibition, adsorption and loss of enzymes and requirement for high amounts of enzymes. Despite substantial effort devoted to reducing the enzyme costs, they are still expensive to produce, with the cost of enzymes accounting for as much as 60% of the process cost, and their action is slow (Wyman 2007). Whole cell saccharification of lignocelluloses to sugars convertible to fuel ethanol can avert these problems.

SUMMARY

Whole cell saccharification of lignocelluloses to sugars using a dual bioreactor system is described in the present invention. An important aspect of using whole microbial cells for the saccharification process is the possibility of secretion of a wide spectrum of synergistic enzymes required for complete degradation of wood waste and inedible grass (lignocelluloses) to fermentable sugars such as glucose and xylose. Other aspects include: (a) elimination of end-product inhibition by accumulation of sugars that are inhibiting to enzymes; and (b) reduction of losses due to enzyme instability, with lignocellulose wastes used directly as inoculum and potential contaminants having the ability to use cellulose as a carbon source, thus contributing to sugar production. In addition, the use of microbial cells offers the potential to lower cost and enhance efficiency by avoiding the enzyme production step required in processes featuring enzymatic hydrolysis. Furthermore, a novel biocatalytic hybrid bioreactor system dedicated to this bioprocess is developed, which embodies recent advances in nanotechnology. This bioreactor system is relatively inexpensive, and can be easily adapted by small-scale producers of fuel ethanol in local communities, especially those involved in agriculture.

Thus the present invention relates the use of natural lignocellulose degrading bacteria for saccharification of lignocellulose, which are enriched from cultures inoculated with paper mill waste water, wood processing waste and soil. A three-member bacterial consortium (TMBC) is selected as a potent microbial inocula for lignocellulose saccharification, and then these bacteria are immobilized on inedible plant fibers, which include, but not limited to, Bermuda grass, switch grass and corn stover.

Further the present invention relates to the design of a dual bioreactor system. Various biocarriers which include, but not limited to, celite, polymer nano arrays and carbon nanotubes coated polyurethane (PU) foam, are used to trap and immobilize enzymes in effluent from the plant fiber bed. One important aspect of immobilization of enzymes in the effluents is increasing enzyme activity and stability. In addition, it offers reduced cost by repeating use of enzyme.

Finally the present invention relates to a process for converting lignocelluloses to fermentable sugars with the dual bioreactor system employing nanotechnology. In this process, microorganisms grow simultaneously with production of an array of enzymes for complete breakdown of lignocelluloses. Sugars are continuously removed eliminating end-product inhibition.

DRAWINGS

The drawings described herein are for illustration purposes only and are not intended to limit the scope of the present disclosure in any way.

FIG. 2 shows the details of the dual reactor system. The first column (D) contains bacterial isolates with entrapped enzymes immobilized on plant waste (inedible grass and corn stover). As the process progresses, some of the enzymes are freed from the bacterial isolate and these cell-free enzymes trickle down, through a fine mesh screen, to the 2nd partition with porous celite. Any cell-free enzymes that 'escape' the celite are further circulated to the second column. The second column is packed with polypyrrole nano arrays, and polyurethane foams coated with layers of carbon nanotubes are placed in between to fix the position of nano-arrays and also to further increase the available surface area. Herein, these cell-free enzymes are trapped within the nano-bristle-brush plates and foams, and begin to accumulate as brought in by the tangential flow.

DESCRIPTION

In the present invention, nineteen lignocellulose-degrading bacteria, purified from cultures inoculated with paper mill wastewater, wood processing waste and soil, have been evaluated for production of enzymes involved in biodegradation of lignocellulose. The isolates produced an array of lignocelluloses-hydrolyzing enzymes. Two isolates (referred to as DB1 and DB2) displayed the highest filter paper cellulase, 27.83 $U \cdot mg^{-1}$ and 31.22 $U \cdot mg^{-1}$, respectively. The highest β-glucosidase activity (18.07 $U \cdot mg^{-1}$) was detected in the culture of isolate DB1. Isolate DB2 produced the highest xylanase activity (103.05 $U \cdot mg^{-1}$) while the highest β-xylosidase activity (7.72 $U \cdot mg^{-1}$) was exhibited by another isolate (DB13). Three isolates including DB1, DB2, and DB7 were selected to compose a three-member bacterial consortium (TMBC) for lignocellulose saccharification.

A new biocatalytic hybrid column reactor system is developed which integrates two columns. The first column is packed with celite, and the second with polymer nanowire arrays spaced with polyurethane foams coated with carbon nanotubes with tremendous surface area. Celite is a commercially available filter material developed using porous diatomite. The major constituent of diatomaceous earth is amorphous $SiO_2$, with minor amounts of other minerals (iron oxide, calcium hydroxide, Mg, Na, Al). Commercial celite is shaped as fine-sized, irregularly shaped porous particles having a large surface area and high liquid absorption capacity. The polymer nano array is fabricated using the membrane-based synthetic approach for templating nanomaterials. The arrays provide the highest specific area-to-volume ratio. It is preferred to use conductive polymers, includes polypyrrole (PPy) and Poly(3,4-ethylenedioxythiophene) (PEDOT). Thus, electrical charge can be applied to the array to enhance the enzyme entrapment. Carbon nanotube coated polyurethane foam is prepared using the method of layer-by-layer self assembly. The preformed polyurethane foam is inert, with coating of carbon nanotube multilayers, the surface area of PU foam can be significantly increased, and the surface can be charged. These nano materials can effectively trap enzymes. The immobilized enzymes are preferred for a continuous process which exhibit better activity and stability when compared with free enzymes.

In a preferred embodiment, the TMBC is mixed with inedible plant fibers and incubated for two hours, thus cells are immobilized on fibers. In a general process, the fiber pre-culture is packed in the top portion of the first column. This is followed with circulation of appropriate mineral elements solution to encourage the colonization of substrates in the bioreactor and to initiate conversion of substrates to sugars. As the process progresses, some of the enzymes are freed from the bacterial isolate, which trickle down through a fine mesh screen to a second portion with porous celite, and some enzyme are physically trapped in celite. Any cell-free enzymes that 'escape' the celite are further circulated to the second column. Herein, these cell-free enzymes are driven by tangential flow into polymer nano-arrays with tremendous surface area, where they are trapped and accumulated. Preferably, this entrapment is enhanced by applying a very small electrical charge to nano-arrays. The solution flows in a zig-zag pattern. Polyurethane foams coated with layers of carbon nanotubes are placed in between the polymer nano-arrays to fix the position of nano-arrays and also to further increase the available surface area. The sugar produced is continuously removed from the columns.

EXAMPLES

Figure 1:
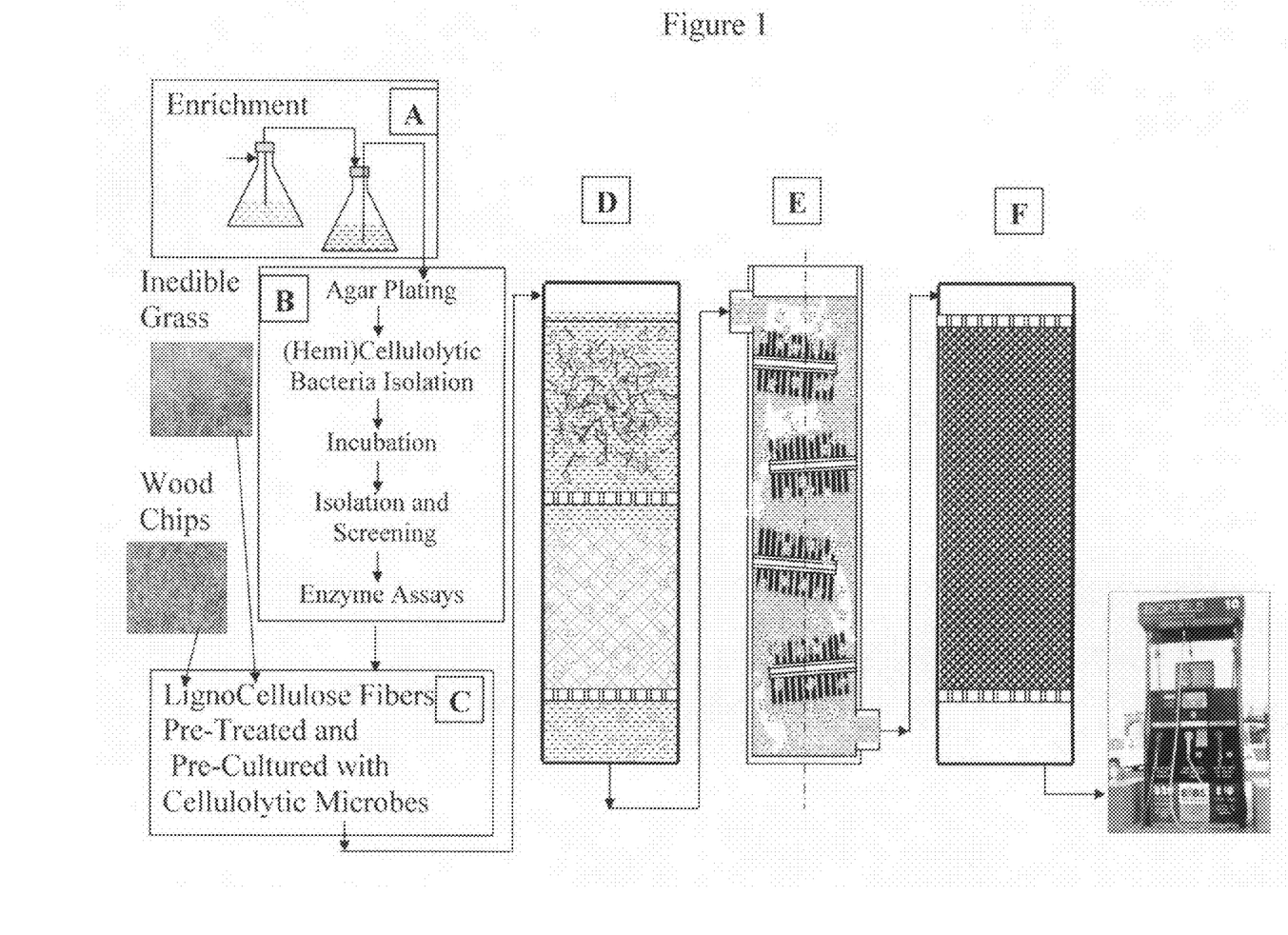
FIG. 1 shows a flowchart of the process used for converting lignocellulose to sugar. Natural lignocellulose degrading bacteria purified from cultures inoculated with paper mill waste water, wood processing waste and soil are enriched, and immobilized on biomass (A, B, and C). A dual biocatalytic hybrid reactor system with high efficiency is developed that uses cellulolytic isolates as biocatalysts (D and E). Biocatalyst support material in the reactors can be celite, polymer nanoarray and PU foams. Additional column F is added for the fermentation of sugars to ethanol.
Figure 2:
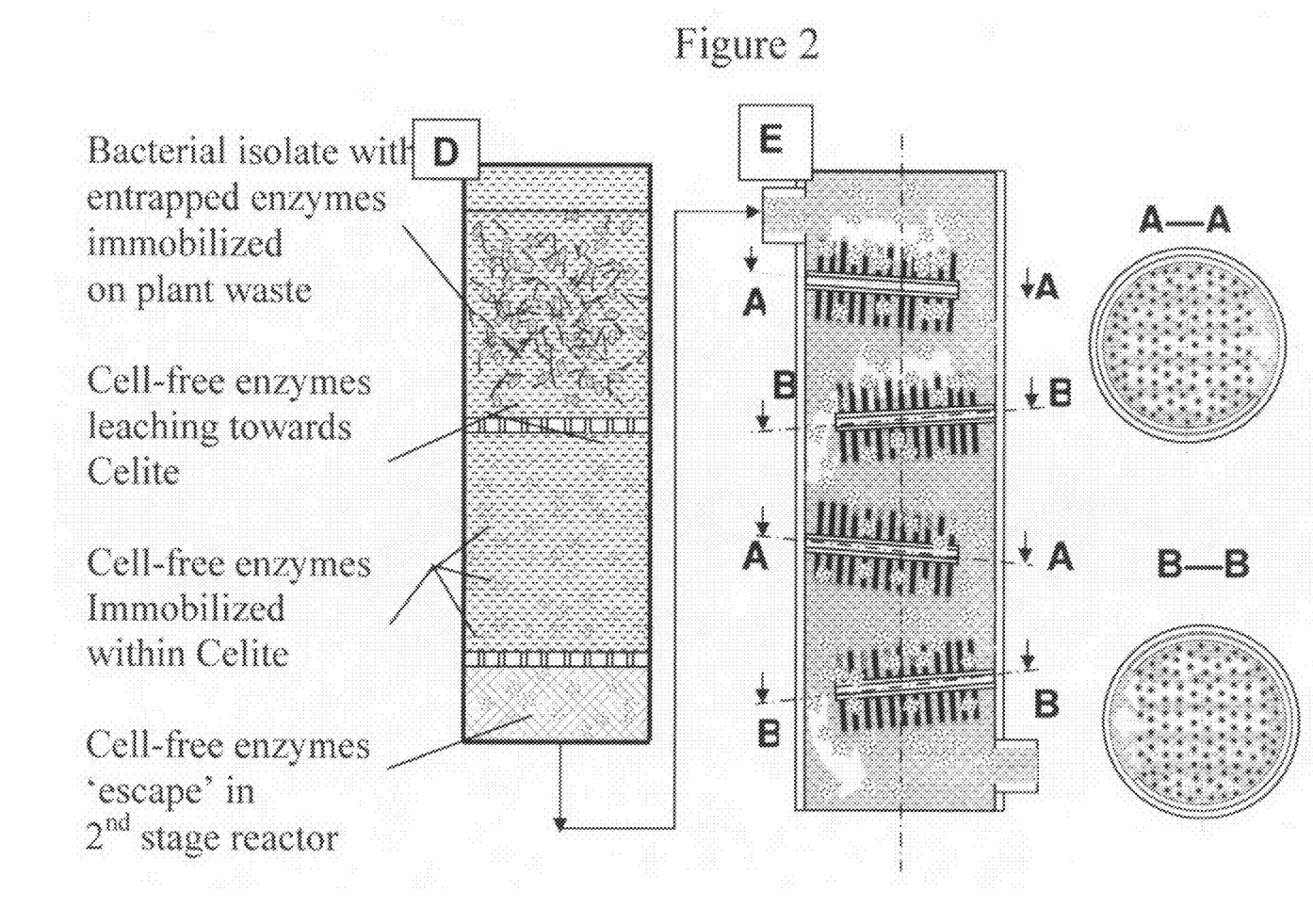

The general flowchart of whole cell saccharification of lignocellulose to sugar using a dual bioreactor system is given in FIGS. 1 and 2.

Example 1

Figure 3:
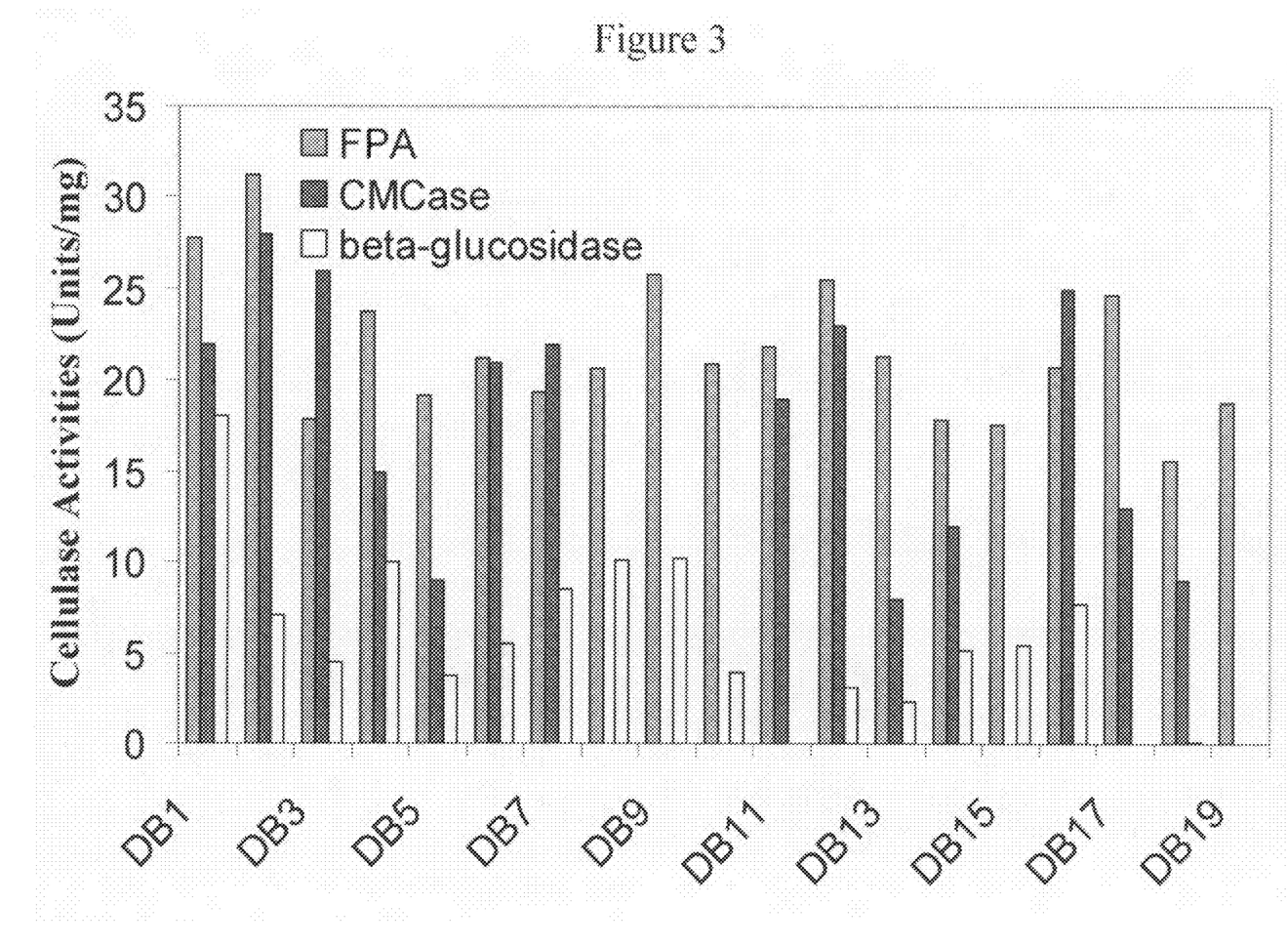
FIG. 3 shows filter paper, Carboxymethylcellulase (CM-Case) and β-glucosidase activities of nineteen batches of bacterial isolates screened.
Figure 4:
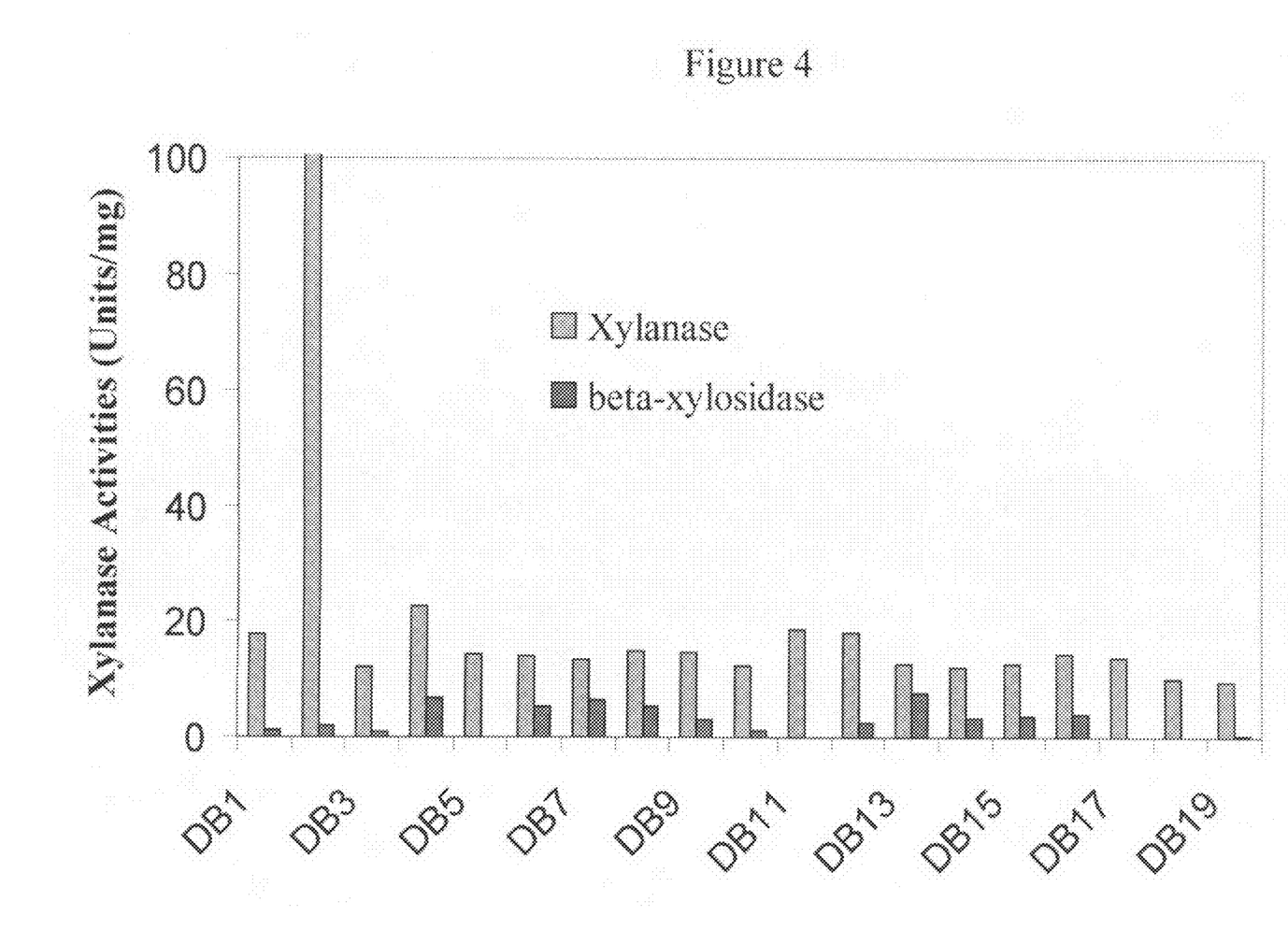
FIG. 4 shows xylanase and β-xylosidase activities of nineteen bacterial isolates screened.

This example shows how to enrich facultatively anaerobic lignocellulose degrading bacteria from natural sources. Samples used for enrichment of facultatively anaerobic lignocellulose degrading bacteria are grassland soil, hardwood compost, pine needle compost, mulched flowerbed soil and paper mill waste water (collected from a waste treatment stage with biological activity). The enrichment basal medium is preferably FTW mineral salts medium which comprised of the following (in g/L): $K_2HPO_4$, 0.225; $KH_2PO_4$, 0.225; $(NH_4)_2SO_4$, 0.225; $MgSO_4 \cdot 7H_2O$, 0.05; $CaCO_3$, 0.005; $FeCl_2 \cdot 4H_2O$, 0.005, and 1 ml of trace elements solution (Focht 1994). Initial pH is adjusted to 7.4 before autoclaving (121° C., 20 min) using aliquots of 1M NaOH. The lignocellulose substrate is 0.25 g steriled pine wood chips and Bermuda grass added to 50 mL steriled FTW enrichment medium in 50 mL centrifuge tubes. Triplicate enrichment media are inoculated with 0.5 g of wood processing waste, soil and paper mill waste water. Enrichment cultures are incubated in an orbital shaker at 28-30° C. for 5 days. Nineteen batches of lignocellulose degrading bacteria are assessed for production of enzymes involved in lignocellulose biodegradation. FIG. 3 shows filter paper, Carboxymethylcellulase (CMCase) and β-glucosidase activities, and FIG. 4 shows xylanase and β-xylosidase activities of nineteen bacterial isolates screened. DB1, DB2 and DB7 are selected to compose a defined three member bacterial consortium (TMBC) for lignocellulose saccharification.

Example 2

Selected TMBC is grown in the enrichment medium in Erlenmeyer flask. 500 ml FTW solution is mixed with 0.5 ml trace element solution, 0.5 g yeast and 0.5 g Bermuda grass, followed with sterilization. 100 mL of TMBC culture solution is added and incubated at 30° C. for 36 hours. The optical density (absorbance at 600 nm) for the resulting culture is in the range of 1.0-1.5. This mixed culture is used for saccharification of lignocelluloses.

Example 3

This example teaches how to fabricate polymer nano array plates as the biocarrier for the reactor. First, a polycarbonate membrane with 0.2 microns pore size is immersed in water for 15 minutes, and then it is secured (clamped) at the interface of two glass tubes. The short tube is filled with 100 mL of 0.2 M aqueous solution of pyrrole monomer, and the longer J-shaped tube is filled with 400 mL of a chemical oxidizer and cross-linker. These two aqueous solutions diffuse towards each other, through the membrane's pores, react, and yield polypyrrole (PPy) nanowires or nanotubes.

Figure 5:
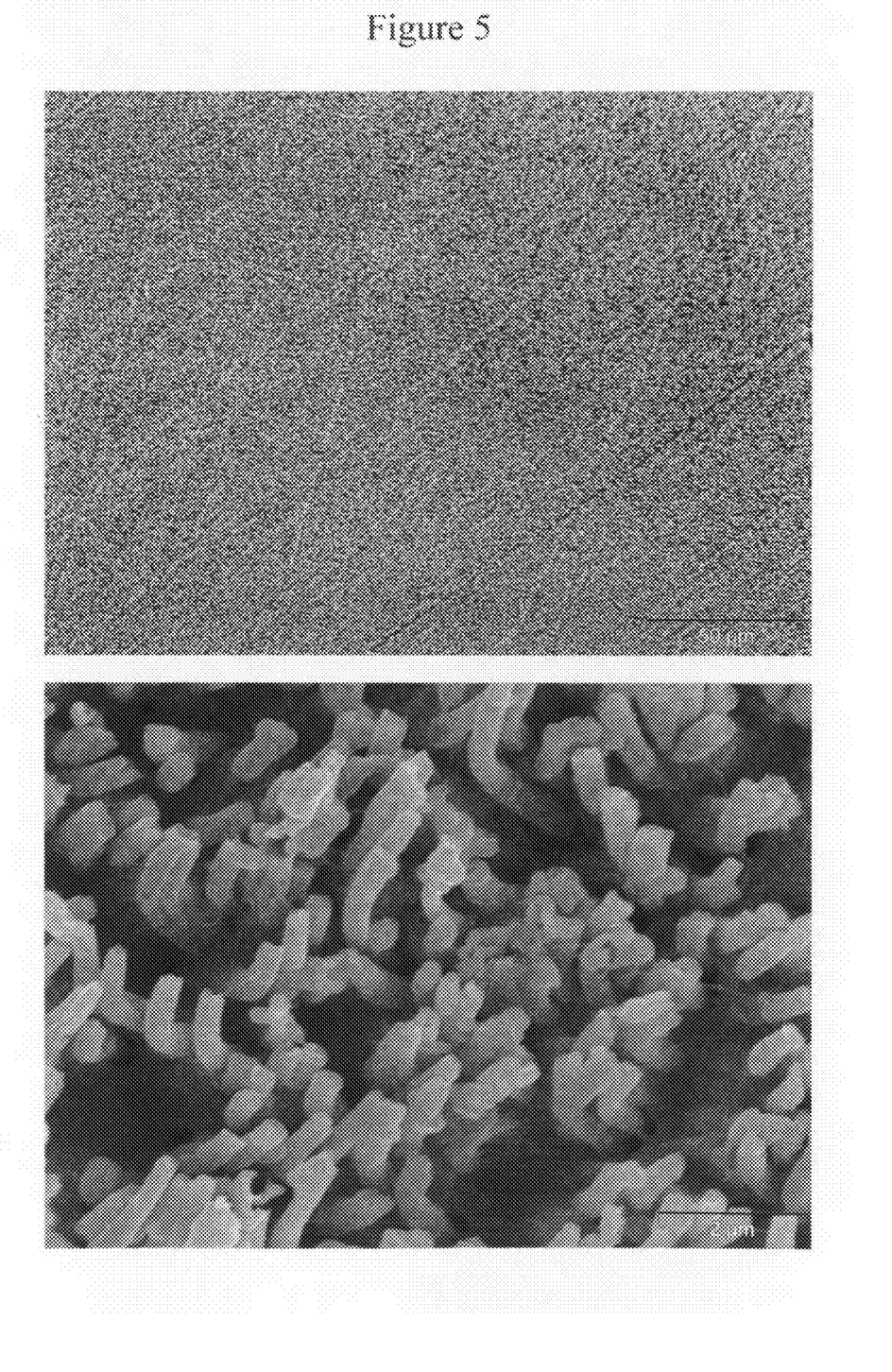
FIG. 5 shows the scanning electron microscope (SEM) images of polypyrrole nano arrays synthesized in house used as biocarrier in the reactors.

In essence, these 100 nm diameter pores are acting like nano-templates for the nascent, nesting polymer within the membrane. As the PPy is formed within and around the membrane, the surrounding solution gradually becomes darkblue-green. The nano-templating is completed in 2-3 hours, at 25±1° C. (room temperature), and as the polymerization continues out of the pores, on the membrane's surface. Next, the membrane is rinsed, and then one side of the membrane was cleaned with chloroform. Then, the other side of the PPy film was rinsed, dried, and subsequently sputter-coated with a 50 nm film of Titanium-Gold in a vacuum deposition chamber. To obtain the nano-fiber array, the polycarbonate template is removed by chloroform rinsing. FIG. 5 shows the SEM images of PPy nano-fiber arrays.

Example 4

Figure 6:
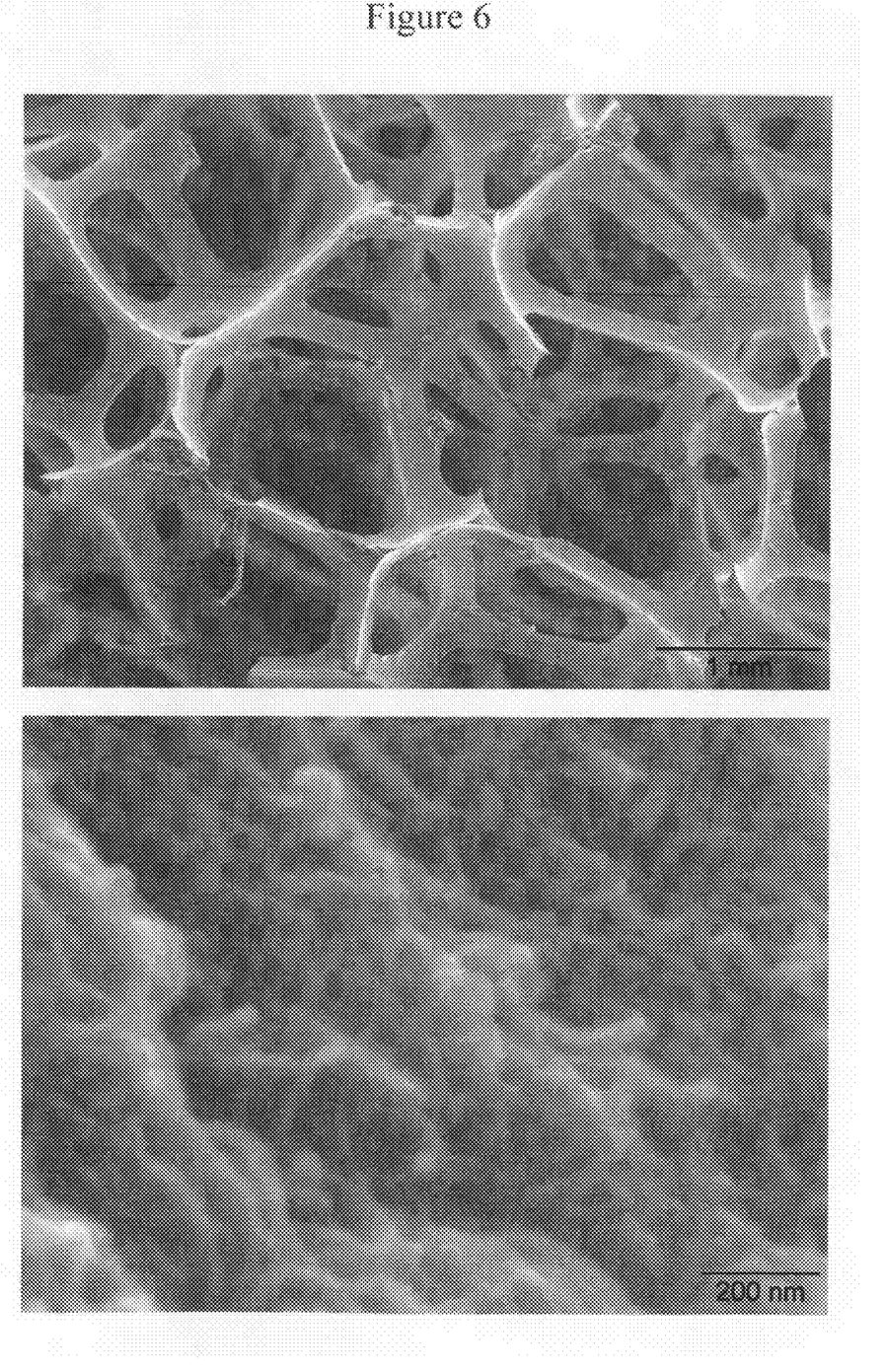
FIG. 6 shows the SEM images of polyurethane foam and carbon nanotubes coated on polyurethane foam which is used as biocarrier in the reactors.

Carbon nanotube coated polyurethane foam used as the biocarrier in the second column is fabricated using the following steps: First polyurethane foam is UV-Ozone treated for 30 mins. 0.1 g of multi-wall carbon nanotube (MWNT) with a diameter of 15 nm and length in the range of 1-5 μm is dispersed in 100 ml 10 mM sulfonated polystyrene (SPS) solution with 0.1 M NaCl by sonication at 200 W for 40 minutes, and then incubated for 24 hrs. The resulting SPS coated MWNTs are filtered using a membrane with pore size of 0.22 μm and washed three times with DI water. SPS coated MWNTs are then redispersed into DI water by sonication at 100 W for 15 minutes. PU foam is dipped in 1 wt % polyethyleneimine (PEI) solution for 1 hr, washed three times with DI water. It is then soaked in MWNT solution for 30 mins, followed with washing with DI water for three times. The PU foam is further coated with a monolayer of poly(diallydimethyl ammonium chloride) (PDAC) by dipping in 20 mM PDAC solution with 0.1 M NaCl for 20 mins, followed by washing with DI water three times. This process is repeated until five bilayers of SPS-MWNT/PDAC are coated on PU foam. FIG. 6 shows the SEM images of five bilayers of MWNT coated PU foam.

Example 5

Figure 7:
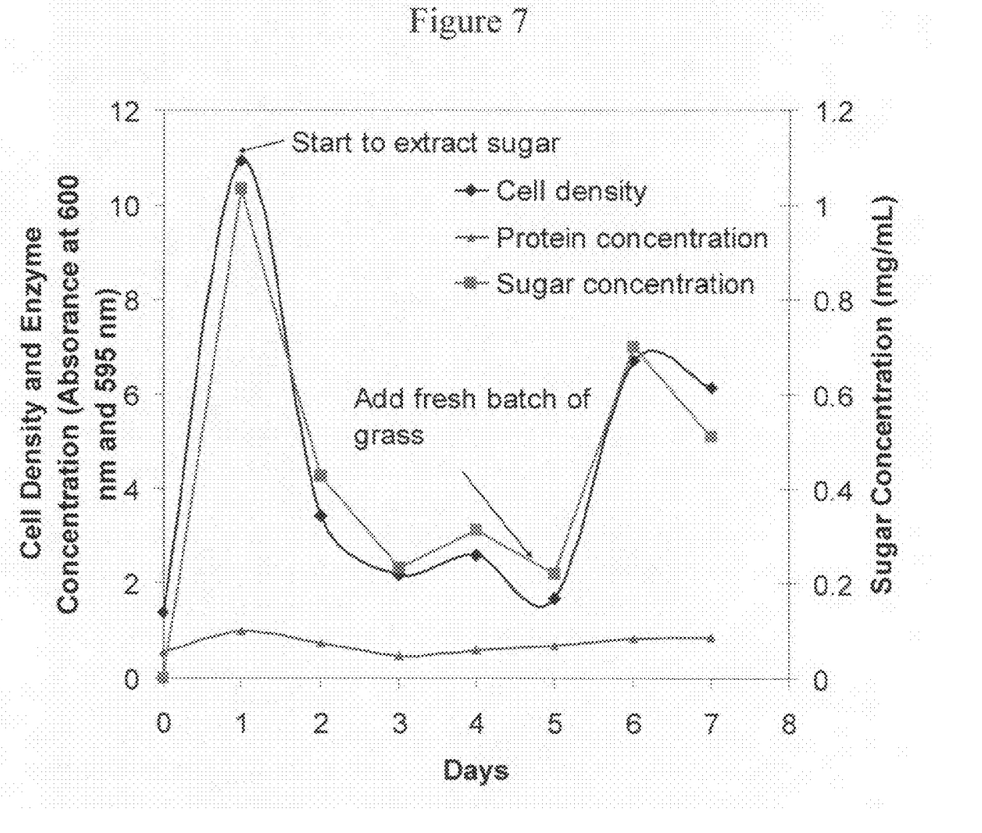
FIG. 7 shows the time course of the hydrolysis of Bermuda grass using the dual reactor system.

Bermuda grass collected from lawn is washed several times with water or not washed to be bioactive if bioprocessed, and dried at room temperature. The grass is cut into 1.0 cm long and further dried at 60° C. under vacuum for 24 hrs before use. 6.0 g of grass is mixed with 150 g of TMBC culture solution and incubated by shaking at the speed in the range of 80-160 rpm for 2 hrs. The cell immobilized grass together with culture solution is packed in the first column with volume of 150 ml. The second column is packed with Celite R635 only. The FTW solution is continuously pumped into the first column at a speed of 6 ml/hour, and sugar is removed continuously. FIG. 7 shows the time course of cell concentration, enzyme and sugar concentration during the process. The total weigh loss of the grass during the process is approximately 30.8%. The conversion of cellulose based on the cellulose composition analysis before and after hydrolysis is 18.8%, but actual sugar collected accounts for 56% of sugar produced.

Example 6

Figure 8:
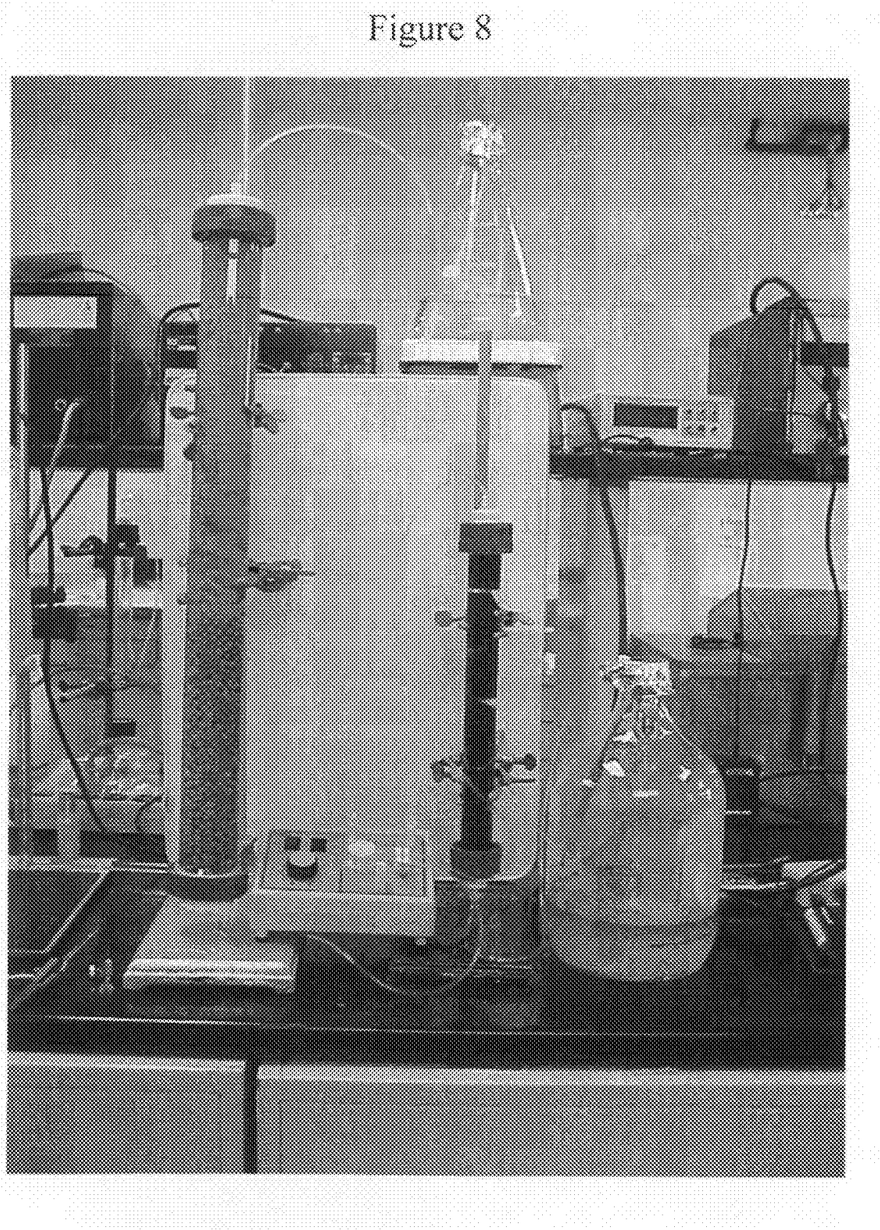
FIG. 8 is a picture of bench top bioreactor system.

A complete design of dual bioreactor system is shown in FIG. 8. 70 g standard corn stover received from National Renewable Energy Laboratory is mixed with 22 ml culture diluted with 1 L FTW solution. The mixture is incubated for 12 hrs. Corn stover is then packed in the top portion of the first column (Volume: 1 L), and 185 g Celite is packed in the bottom portion of the column. The second column (125 mL) is packed with 5 plates of polypyrrole nano array spaced with PU foam. The FTW solution is continuously pumped into the columns and the sugar produced is removed.

What is claimed is:

1. A process for whole cell saccharification of lignocelluloses to sugars using a dual bioreactor system comprising the following steps:
    immobilizing lignocellulose degrading bacteria on biomass, wherein the bacteria constitute a bacterial consortium selected from natural lignocellulose degrading bacteria enriched from cultures inoculated with paper mill waste water, wood processing waste or soil;
    packing biomass with culture in the top partition of the first column reactor;
    packing celite in the bottom partition of the first column reactor, which is separated from biomass by a fine screen;
    continuously filling the first column with the enrichment basal medium, as the process progresses, some of the enzymes freed from the bacterial isolate trickling down to the second partition with porous celite, and getting trapped in celite;
    further circulating the product stream from the first column to a second column reactor, the second reactor comprising nano biocarriers, providing increased surface area for enzyme immobilization; and
    collecting sugar from the second reactor to be fermented to ethanol.

2. The process of claim 1, wherein the biomass is Bermuda grass, switch grass, wood chips or corn stover.

3. The process as described in claim 1, wherein the enrichment basal medium is preferably FTW mineral salts medium, which comprised of the following (in g/L): $K_2HPO_4$, 0.225; $KH_2PO_4$, 0.225; $(NH_4)_2SO_4$, 0.225; $MgSO_4.7H_2O$, 0.05; $CaCO_3$, 0.005; $FeCl_2.4H_2O$, 0.005, and 1 ml of trace elements solution.

4. The process as described in claim 1, wherein the immobilized cells secrete a wide spectrum of enzymes for lignocellulose degradation which include cellulase, β-glucosidase, xylanase, and β-xylosidase.

5. The process as described in claim 1, wherein the product stream from the first reactor contains sugars, oligosaccharides, and enzymes, wherein the sugars comprise glucose and xylose, and wherein the oligosaccharides comprise short chains of glucose and xylose.

6. The process as described in claim 1, wherein the second column reactor has two functions:
   immobilizing enzyme on nano biocarriers for repeated uses; and
   further reducing oligosaccharides to glucose and xylose.

7. The process as described in claim 6, wherein the nano biocarriers are polymer nano-arrays and polyurethane foam coated with carbon nanotubes.

* * * * *